United States Patent
Ott et al.

(10) Patent No.: US 8,551,050 B2
(45) Date of Patent: Oct. 8, 2013

(54) DEVICE AND METHOD FOR CONTROLLING THE FLOW RATE OF EVACUATING SURGICAL VAPOR AND MIST FROM A BODY CAVITY

(75) Inventors: Douglas E. Ott, Macon, GA (US); Nathaniel V. Tran, Apple Valley, MN (US)

(73) Assignee: Lexion Medical, LLC, St. Paul, MN (US)

( * ) Notice: Subject to any disclaimer, the term of this patent is extended or adjusted under 35 U.S.C. 154(b) by 110 days.

(21) Appl. No.: 13/157,561

(22) Filed: Jun. 10, 2011

(65) Prior Publication Data

US 2012/0316512 A1    Dec. 13, 2012

(51) Int. Cl.
*A61M 5/178*      (2006.01)

(52) U.S. Cl.
USPC ...... 604/167.03; 604/23; 604/26; 604/167.05

(58) Field of Classification Search
USPC ............................ 604/23–26, 167.03, 167.05
See application file for complete search history.

(56) References Cited

U.S. PATENT DOCUMENTS

| | | |
|---|---|---|
| 5,199,944 A | 4/1993 | Cosmescu |
| 6,592,543 B1 | 7/2003 | Wortrich et al. |
| 7,789,946 B2 | 9/2010 | Schultz et al. |
| 7,854,724 B2 | 12/2010 | Stearns et al. |
| 2002/0128603 A1 | 9/2002 | Booth et al. |
| 2010/0185139 A1 | 7/2010 | Stearns et al. |
| 2010/0241061 A1 | 9/2010 | Ott et al. |

*Primary Examiner* — Emily Schmidt
(74) *Attorney, Agent, or Firm* — Winthrop & Weinstine, P.A.

(57) ABSTRACT

Devices and methods for vacuum-assisted removal of surgically contaminated gas from an insufflated body cavity, the contaminants comprising smoke, aerosols, vapor, mist and the like generated during surgical procedures in order to clear the surgeon's vision of the surgical site and prevent exposure of the surgical staff to the gas. One embodiment of the present invention comprises a series of flow restriction devices to enable stepping down of the flow rate generated by an external vacuum. This reduced flow rate allows safe yet rapid removal of the toxic and vision-obstructing surgical byproducts from the patient's body cavity. The initial flow restriction device may comprise a perforated trocar sleeve in fluid communication with the vacuum source that allows retention of the surgical instrument within the trocar's inner lumen with concurrent smoke removal. The flow rate is infinitely variable, adjustable and selectable using a flow control adjuster comprising a smoothly varying orifice.

6 Claims, 9 Drawing Sheets

DEVICE AND METHOD FOR CONTROLLING THE FLOW RATE OF EVACUATING SURGICAL VAPOR AND MIST FROM A BODY CAVITY

BACKGROUND OF THE INVENTION

1. Field of the Invention

The invention relates to devices and methods for controlling the flow rate of evacuation of contaminated gas from a surgical cavity during certain surgical procedures.

2. Description of the Related Art

During the performance of certain surgical procedures a surgeon may need to use a needle or a trocar device to deliver fluid into a body cavity, or a portion of a body, for the purposes of inflating or distending the body cavity to make it easier to see and perform the desired treatment. Common procedures in which insufflation is used include any type of an endoscopic surgical procedure, as well as laparoscopic or thoracoscopic surgical procedures performed in the abdominal or thoracic body cavities, respectively. In these procedures a blind incision, for example, or a Verres needle may be used to initially traverse the skin and tissue layers until the body cavity is entered for the purpose of passing a pressurized fluid, either a gas or a liquid, into the body cavity.

When a blind incision is made, a standard trocar assembly may then be passed through the incision and into the body cavity, whereupon the desired fluid is passed through the trocar into the body cavity. If a Verres needle has been used to penetrate the body cavity, an external gas source is attached to a proximal end of the needle projecting outwardly from the body cavity. Under pressure, the desired fluid flows through the needle and is delivered into the body cavity for inflating the body cavity. In either instance, this process is known as insufflation, in which the desired fluid, as well as any other substances, which may include drugs and anesthetics, is passed under pressure into the body cavity. A commonly used gas for this procedure is carbon dioxide. Depending on the patient's size, medical condition, the procedure to be performed, and the surgeon's preference, the gas is flowed into the body cavity at a rate of from 0.1 to 20 liters per minute.

As described, physicians may use trocar assemblies for the purposes of passing a pressurized fluid within a body cavity. Known trocar assemblies have a solid outer sheath or a sleeve that is sized and shaped to allow passage through the incision and tissue layers of a body so that the sleeve penetrates at least partially into the body cavity. This is accomplished by passing an elongate central retracting piercing element, referred to as a trocar or an obturator, through the sleeve and then passing the sleeve and the trocar together through the tissue. Once the sleeve is passed into the body cavity to the desired depth, the trocar is withdrawn from the sleeve.

During the insufflation process the pressurized fluid distends the body cavity to move the tissue layers outwardly of the body to create sufficient space in the cavity to observe and/or treat the organs and/or body structures therein. Once the body cavity is sufficiently distended and the obturator of the trocar is withdrawn from the lumen of the trocar sleeve, surgical instruments are typically passed through the lumen, while fluid continues to flow. This allows the surgeon to visualize the contents of the body cavity and proceed with the desired diagnostic and/or surgical procedures without damaging the remaining tissues, organs, or body structures within the body cavity.

Use of the surgical tools to cut body tissue generates contaminants and byproducts comprising smoke, aerosols, vapor and mist, etc., that disrupts the surgeons view of the surgical site and may present health risks to the surgical staff if exposed. Past attempts to safely and effectively remove the contaminated gas include simply releasing the smoke into the surgical environment, exposing the surgical team to the smoke and its contaminants. Other solutions comprise using the pressure in the surgical cavity to drive gas outflow, and filtration. This is unsatisfactory because reliance on the surgical cavity pressure may often be insufficiently effective in removing the contaminated gas as quickly as desired.

Other solutions use a vacuum source in line and in fluid communication with the surgical cavity. These solutions must be very controlled in restricting the fluid flow rate so as to permit a rapid gas/smoke removal while reinsufflating the surgical cavity to compensate for the gas/smoke that is removed in order to maintain sufficient pressure and distension within the surgical cavity. The abdominal cavity of the average patient comprises approximately two liters in volume, thus, a relatively low flow rate is required in order to remove smoke from the cavity. The smoke removal procedure may require a relatively rapid and full gas exchange within the surgical cavity in order to remove the smoke. Such gas/smoke removal should be done as quickly as possible in order to allow the surgeon vision of the site and to expedite the surgical procedure. A typical wall vacuum comprises relatively high flow rates, for example and without limitation between 40 to 100 liters per minute or more, which requires that flow restrictions be placed along the fluid conduit in order to bring the flow rate in the surgical cavity to within the range of between 0 to 30 liters per minute. Known solutions comprise providing a filter with sufficient resistance to reduce the flow rate of the fluid passing therethrough and/or predetermined orifice sizing combinations placed in fluid communication with the vacuum and surgical cavity. These solutions rely on manipulation of the filter composition and size and/or predetermined and fixed sized orifice combinations in order to achieve a safe flow rate.

Thus, all known devices provide predetermined flow rates; no known device or method provides infinitely variable selection of gas evacuation flow rates.

The present invention overcomes these deficiencies.

BRIEF SUMMARY OF THE INVENTION

Devices and methods for vacuum-assisted removal of surgically contaminated gas from an insufflated body cavity, the contaminants comprising smoke, aerosols, vapor, mist and the like generated during surgical procedures in order to clear the surgeon's vision of the surgical site and prevent exposure of the surgical staff to the gas. One embodiment of the present invention comprises a series of flow restriction devices to enable stepping down of the flow rate generated by an external vacuum. This reduced flow rate allows safe yet rapid removal of the toxic and vision-obstructing surgical byproducts from the patient's body cavity. The initial flow restriction device may comprise a perforated trocar sleeve in fluid communication with the vacuum source that allows retention of the surgical instrument within the trocar's inner lumen with concurrent smoke removal. The flow rate is infinitely variable, adjustable and selectable using a flow control adjuster comprising a smoothly varying orifice.

The figures and the detailed description which follow more particularly exemplify these and other embodiments of the invention.

BRIEF DESCRIPTION OF THE DRAWINGS

The invention may be more completely understood in consideration of the following detailed description of various embodiments of the invention in connection with the accompanying drawings, which are as follows.

DETAILED DESCRIPTION OF THE INVENTION, INCLUDING THE BEST MODE

Figure 1A:
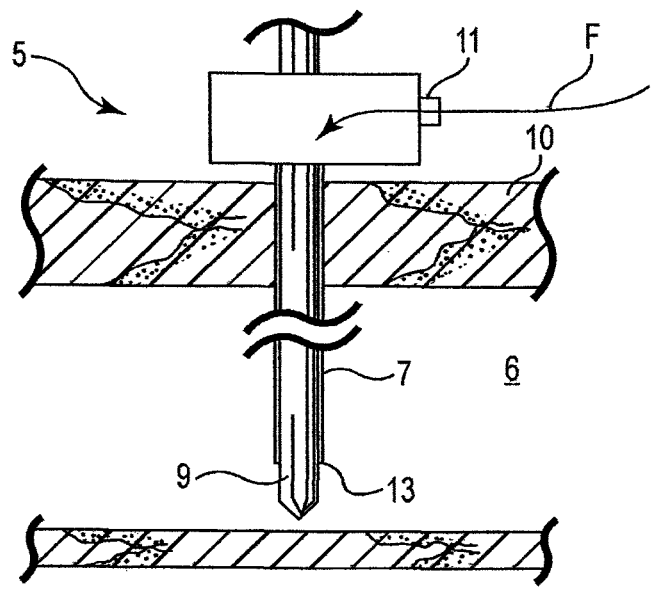
FIGS. 1A and B are partial cross-sectional illustrations of a known type of trocar sleeve.

While the invention is amenable to various modifications and alternative forms, specifics thereof are shown by way of example in the drawings and described in detail herein. It should be understood, however, that the intention is not to limit the invention to the particular embodiments described. On the contrary, the intention is to cover all modifications, equivalents, and alternatives falling within the spirit and scope of the invention.

An example of the known types of trocar assemblies is illustrated in FIGS. 1A and B, in which a known trocar assembly 5 is shown being used to gain access to a body cavity 6. The trocar assembly is comprised of a solid outer sheath or sleeve 7, the sleeve 7 defining a central lumen (not shown) therethrough. A trocar 9, comprising a distal piercing element, is slidably disposed within the lumen of the sleeve 7. The trocar 9 is used together with the trocar sleeve 7 to pierce the skin, the subcutaneous tissue, the fascia, the muscle, and the innermost layer of the cavity, collectively referred to as 10, to include the parietal peritoneum or the pleura, respectively, for either the abdominal or chest cavities.

Figure 1B:
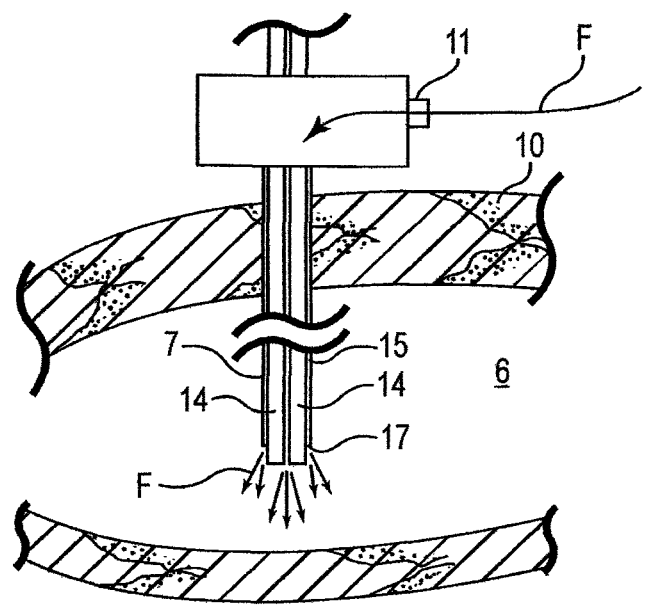

As shown in FIG. 1B, removal of the trocar 9 after accessing the body cavity 6 allows various instruments 14, to include light sources, viewing scopes, graspers, manipulators, irrigators, suction devices, sutures, lasers, coagulators, biopsy devices, clip appliers and needle holders, may be placed through the lumen of the trocar sleeve 7 and into the body cavity 6 for the treatment or procedure to be performed.

As illustrated, the trocar assembly 5 is inserted into the body cavity, a pressurized fluid "F" from an external source, which may be a gas or a liquid bearing drugs, anesthetics, or other substances placed or mixed within a pharmaceutically acceptable carrier, or any combination thereof, is commonly passed through the access port 11 and transported into the body cavity through the distal end 13 of the trocar sleeve. It is commonplace in procedures of this type that the fluid F will also continue to be passed into the body cavity once the trocar is removed. The access port 11 extends from the proximal end of the trocar sleeve 7 exposed above the skin of the patient.

Once the body cavity is sufficiently distended with pressurized fluid F, the surgeon may then view the surgical site and use lasers, ultrasonic tissue fragmentation devices and/or electrocautery devices and the like for cutting of tissues and/or blood vessels during the surgical procedure. These cutting processes produce undesirable contaminants comprising potentially contaminated smoke, aerosols, vapor, mist and other undesirable byproducts that can cloud or obstruct the surgeon's view of the operative site. The gas within the surgical cavity thus likely contains toxic and unpleasant substances that could expose the surgical staff to a health risk and disrupts the surgeon's view of the surgical site; therefore, the contaminated gas must be safely and efficiently removed from the surgical cavity.

Because, as illustrated in FIG. 1B, the known trocar sleeve 7 will typically have at least one surgical instrument and/or a viewing device placed within its lumen throughout the surgical procedure, the cross-sectional area 15 of the unobstructed lumen available for removal outflow of the smoke, is markedly reduced. The contaminated evacuated gas, i.e., smoke is forced to flow out of the cavity through a relatively small opening 17 in the distal end of the trocar sleeve, then between the outer surface of the instrument(s) within the lumen and the internal surface of the trocar sleeve, which restricts the amount of contaminated fluid, i.e, smoke that may be passed through the trocar sleeve.

Figure 2:
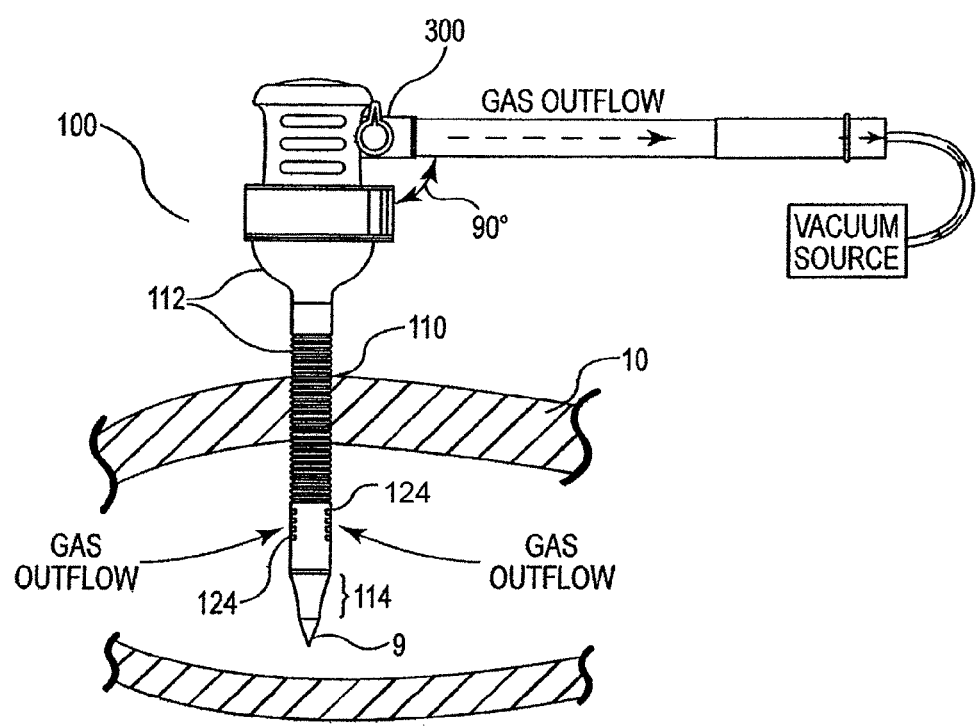
FIG. 2 is a side view of one embodiment of the present invention.
Figure 3:
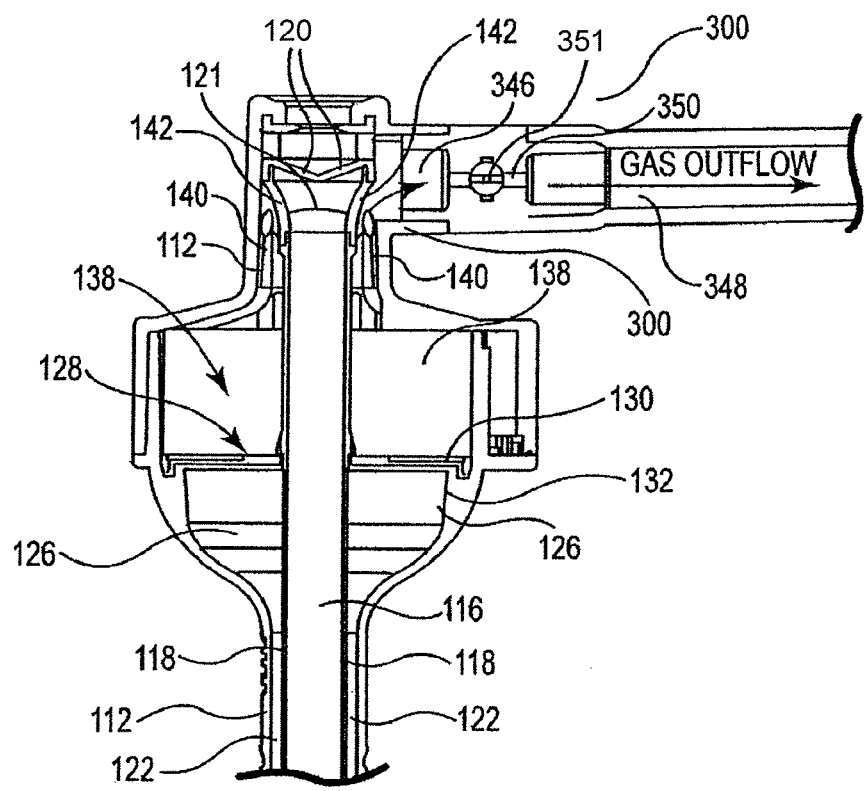
FIG. 3 is a cross section of one embodiment of the present invention.
Figure 3:
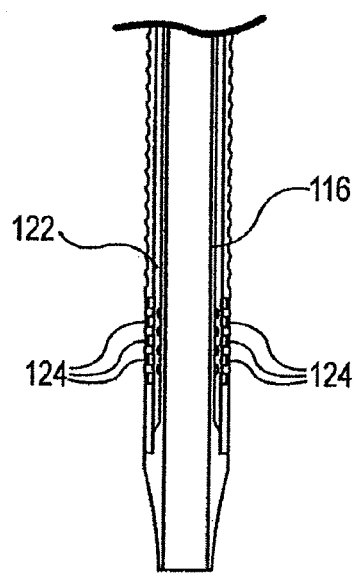
Figure 4:
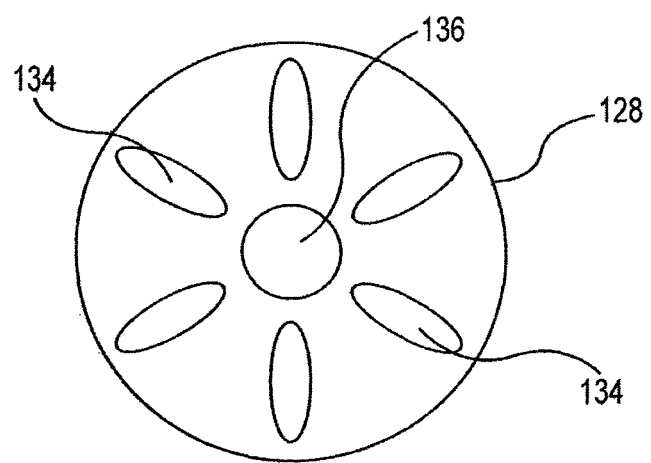
FIG. 4 is a bottom view of one embodiment of a restrictor plate of the present invention.

FIGS. 2 and 3 illustrate one embodiment of a dual lumen gas evacuation device 100 of the present invention inserted through the skin, the subcutaneous tissue, the fascia, the muscle, and the innermost layer of the cavity 10 as described supra. Generally, an elongate trocar sleeve 110 is defined by a housing wall 112 which may be formed of a rigid or resilient plastic, from a metal, or of any desired material suitable for use as a trocar sleeve 110. In general, what is required is that the housing and other elements of the various embodiments of the present invention be constructed of material approved by the United States Food and Drug Administration for use in surgical procedures, that the material(s) be durable, and capable of being completely sterilized for subsequent re-use. It is also anticipated that the inventive device may be constructed as a disposable single-use device, i.e., without need for resterilization and re-use.

The trocar sleeve 110 comprises a distal tapered section 114 to assist with ease of access to the body cavity 6. An inner-most lumen or working channel 116 is defined by a working channel wall 118 disposed within the trocar sleeve 110 and provides a working channel 111 comprising access to the surgical or body cavity 6 through which the surgeon may introduce instruments for communication within the surgical cavity 6. In addition, the working channel 116 slidingly receives a trocar 9, as illustrated in FIG. 2 and which is similar to that illustrated in FIG. 1A, wherein the trocar tip 9 is extending distally beyond the distal end of the trocar sleeve 110. The preferred working channel lumen 116 may be sized to admit a 5 mm diameter instrument, though additional embodiments comprise a working channel lumen 116 that can accommodate instruments therein that range from 3 mm to 14 mm in diameter. As those skilled in the art will readily recognize, the trocar sleeve 100, and the working channel 116, may also be adapted in length to accommodate certain procedures. For example, bariatric laparoscopic procedures may benefit from a longer trocar sleeve 110 and working channel 116 according to the present invention's various embodiments. However, it is important to understand that the size and shape of the present invention is not limited to laparoscopy, e.g., and may, therefore, be adapted and used in other procedures in various embodiments of the present invention.

At least two valves 120, 121 may be in operative communication with the working channel 116 to allow access to the surgical cavity 6 while restricting outflow of the contaminated surgically generated gas to the extent possible through the working channel 116. In the illustrated embodiment the duckbill valve 120, prevents evacuation of contaminated gases from the body cavity when an instrument is absent from the working channel 116. The tool seal valve 121, illustrated as a self-sealing elastomeric valve as is known in the art, prevents evacuation of contaminated gases from the body cavity when an instrument is inserted in the working channel 116. Other types of valves 120 are known in the art; each of these valve types are within the scope of the present invention.

The evacuating gas exits the filtration element 138 and enters the upper region 140 of the secondary lumen 122, defined by outer housing 112 which is in fluid communication with the upper chamber 126, the restrictor plate flow ports 134, the secondary lumen 122 and the gas evacuation ports 124. The working channel wall 118 within the upper region 140 of the secondary lumen 122 comprises a radiused or curved section 142 which directs the evacuating gas radially outward toward the outer housing wall 112 within the upper region 140 of the secondary lumen 122, thereby slowing the flow rate of the evacuating gas and generating a turbulent environment as this radially directed gas impacts the housing wall 112 within the upper region 140 of the secondary lumen 122 and rebounds therefrom and flowing directly into the oncoming evacuating gas that has exited from the filtration element 138. This turbulence further slows the flow rate of the evacuating gas.

The evacuating gas will eventually find an outlet from the turbulent environment in the upper region 140 of the secondary lumen 122. A flow regulation assembly 300 is in operative and fluid connection and communication with the upper region 140 of the secondary lumen 122, at an angled connection, the preferred connection will comprise substantially a right angle as illustrated, though other angled connections are within the scope of the present invention. The fluid regulation assembly 300 comprises a proximal gas outflow lumen 346 and a distal gas outflow lumen 348, each comprising a diameter and a flow regulator lumen 350 disposed between the proximal and distal gas outflow lumens 346, 348 and further comprising a diameter. The flow regulation lumen 350 diameter is smaller than both of the diameters of the proximal and distal gas outflow lumens 346, 348. The flow regulation lumen 150 is in operative and fluid communication with the proximal and distal outflow lumens 146, 148.

Figure 5:
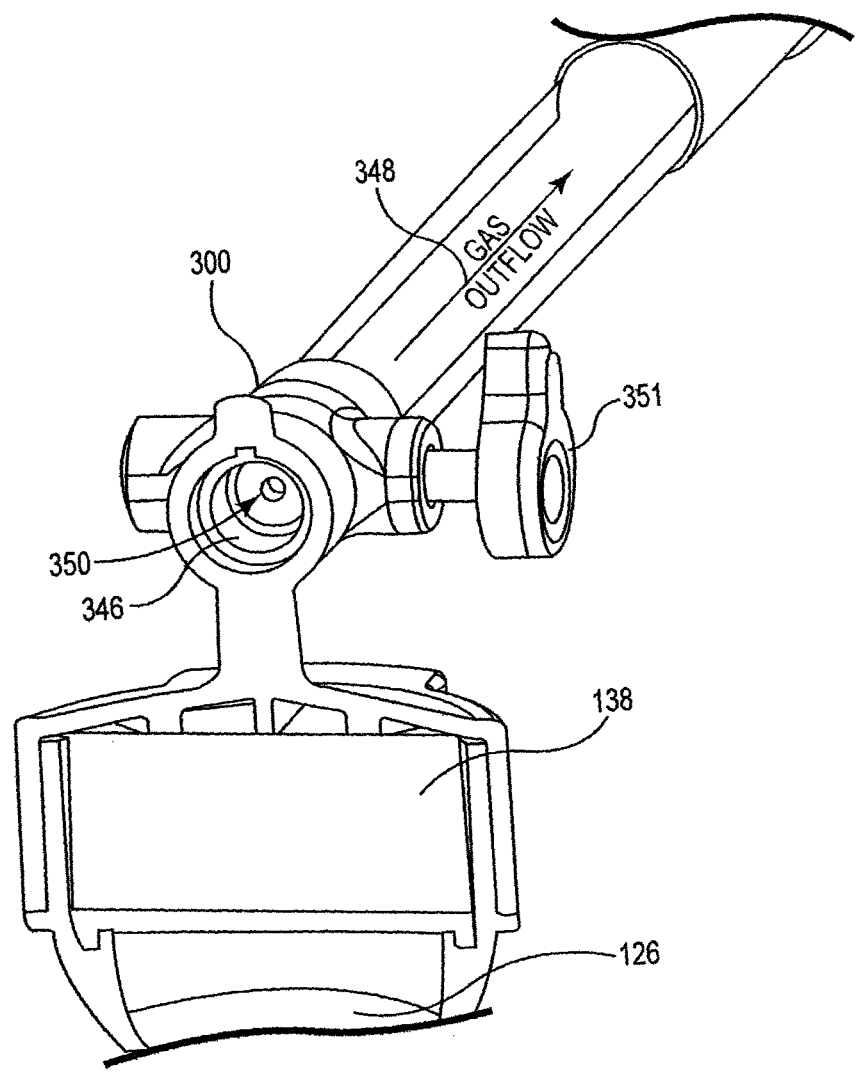
FIG. 5 is a partial cross-sectional view of one embodiment of the present invention.

The fluid regulation assembly 300 is further illustrated in a partial cross-section and broken away view in FIG. 5, wherein the proximal gas outflow lumen 346 and the flow regulator lumen 350 are shown in relation to the cross-sectional illustration the filtration element 138 and the upper chamber 126. The working channel 116 and the upper region of the secondary lumen 140 are not shown in FIG. 5 to better illustrate the relationship between the proximal gas outflow lumen 346 and the flow regulation assembly lumen 350. Thus, the proximal gas outflow lumen 346 is shown broken away from the point of operative and fluid communication and connection with the upper region of the secondary lumen 140 described supra.

The evacuating gas exits the filtration element 138 and enters the upper region of the secondary lumen 140, defined by outer housing 112 which is in fluid communication with the upper chamber 126, the restrictor plate flow ports 134, the secondary lumen 122 and the gas evacuation ports 124. The working channel wall 118 within the upper region of the secondary lumen 140 comprises a radiused or curved section 142 which directs the evacuating gas radially outward toward the outer housing wall 112 within the upper region of the secondary lumen 140, thereby slowing the flow rate of the evacuating gas and generating a turbulent environment as this radially directed gas impacts the housing wall 112 within the upper region of the secondary lumen 140 and rebounds therefrom and flowing directly into the oncoming evacuating gas that has exited from the filtration element 138. This turbulence further slows the flow rate of the evacuating gas.

The evacuating gas will eventually find an outlet from the turbulent environment in the upper region of the secondary lumen 140. A flow regulation assembly 300 is in operative and fluid connection and communication with the upper region of the secondary lumen 140, at an angled connection, the preferred connection will comprise substantially a right angle as illustrated, though other angled connections are within the scope of the present invention. The fluid regulation assembly 300 comprises a proximal gas outflow lumen 346 and a distal gas outflow lumen 348, each comprising a diameter and a flow regulator lumen 350 disposed between the proximal and distal gas outflow lumens 346, 348 and further comprising a diameter. The flow regulation lumen 350 diameter is smaller than both of the diameters of the proximal and distal gas outflow lumens 346, 348. The flow regulation lumen 150 is in operative and fluid communication with the proximal and distal outflow lumens 146, 148.

The fluid regulation assembly 300 is further illustrated in a partial cross-section and broken away view in FIG. 5, wherein the proximal gas outflow lumen 346 and the flow regulator lumen 350 are shown in relation to the cross-sectional illustration the filtration element 138 and the upper chamber 126. The working channel 116 and the upper region of the secondary lumen 140 are not shown in FIG. 5 to better illustrate the relationship between the proximal gas outflow lumen 346 and the flow regulation assembly lumen 350. Thus, the proximal gas outflow lumen 346 is shown broken away from the point of operative and fluid communication and connection with the upper region of the secondary lumen 140 described supra.

Disposed within the flow regulation assembly lumen 350 is a flow regulator 351 that may be actuated to allow fluid communication with the gas evacuation ports 124 and surgical cavity 6 and a downstream external vacuum and to allow fluid communication through the system to the gas evacuation ports 124 and the surgical cavity 6 as described herein. Thus, the flow regulation assembly 300 of the present invention provides a plurality of "ON" settings comprising selectable "LOW" flow rate and "MAX" flow rate settings, with an infinitely variable selectable flow rates therebetween, designated herein as "MID" flow rate settings. The flow regulation assembly 300 and the flow regulator 351 will be discussed in detail infra.

Thus, the dual lumen embodiment provides a fluid conduit that provides a pathway for the evacuating gas from the bodily cavity to a container (not shown) for proper disposal, driven by vacuum pressure provided by an external vacuum source in fluid communication and operative connection with the fluid conduit while allowing the surgeon full access to the surgical cavity 6 through the working channel 116. The structures along the fluid conduit are designed to provide an overall flow rate reduction at the gas evacuation ports 124 and within the surgical cavity 6, necessary to prevent unwanted and potentially damaging effects that may be induced by the relatively high pressure of the external vacuum source as discussed infra.

As the evacuating gas is urged via the external vacuum source further downstream within the fluid conduit, passing through the restrictor plate flow port(s) 134, it encounters the gas filtration element 138. After exiting the gas filtration element 138, the evacuating gas enters the upper region 140 of the secondary lumen 122 and ultimately generating a turbulent environment as the gas encounters the curved region of the working channel wall 142 and is radially urged against the housing wall of the upper region 140 of the secondary lumen 122, rebounding from that impact only to encounter incoming evacuating gas exiting from the filtration element 138. Ultimately, the gas finds a release from this turbulent environment through the fluid regulation assembly 300 which is in operative and fluid communication and angled, preferably 90 degree angled though other angles are within the scope of the present invention, connection with one radial region of the upper region 140 of the secondary lumen 122. As can be seen in FIG. 3, some of the evacuating gas that encounters the working channel's curved surface will be urged radially into the fluid regulation assembly, specifically the proximal gas outflow lumen 346 initially, thereby escaping the turbulent environment.

The vacuum pressure thus ultimately urges the outflowing contaminated gas to make an angled turn into the fluid regulation assembly 300, entering the proximal gas outflow lumen 346 which may comprise a smaller volume than the upper region of the evacuating gas conduit. The contaminated gas then flows through the reduced diameter flow regulation lumen 350, encountering the flow regulation lumen 350 and flowing therethrough at a variably selectable flow rate if the flow regulator 352 is actuated, i.e., in an "ON" position. Once through the flow regulation lumen 350, the contaminated gas then enters the distal gas outflow lumen 348 comprising a diameter larger than the diameter of the flow regulation lumen 350. Ultimately, the contaminated gas may be evacuated to a waste reservoir or otherwise disposed of.

First, in response to the vacuum pressure, the evacuating gas is urged into the plurality of gas evacuation ports 124 and into the secondary lumen 116. The secondary lumen 116 comprises a lower region of substantially constant diameter and volume, wherein the gas is urged under pressure upward through the constant diameter region until reaching the enlarged chamber 126, comprising a cross-sectional volume that is larger than any given cross sectional volume of the secondary lumen 116. The enlarged chamber 126 comprises the restrictor plate 128 comprising a through-hole for the working channel 136 to pass through and a plurality, or at least one, restrictor plate flow ports 134, through which the evacuating gas flows.

As the evacuating gas is urged via the external vacuum source further downstream within the fluid conduit, passing through the restrictor plate flow port(s) 134, it encounters the gas filtration element 138. After exiting the gas filtration element 138, the evacuating gas enters the upper region of the secondary lumen 140 and ultimately generating a turbulent environment as the gas encounters the curved region of the working channel wall 142 and is radially urged against the housing wall of the upper region of the secondary lumen 140, rebounding from that impact only to encounter incoming evacuating gas exiting from the filtration element 138. Ultimately, the gas finds a release from this turbulent environment through the fluid regulation assembly 300 which is in operative and fluid communication and angled, preferably 90 degree angled though other angles are within the scope of the present invention, connection with one radial region of the upper region of the secondary lumen 140. As can be seen in FIG. 3, some of the evacuating gas that encounters the working channel's curved surface will be urged radially into the fluid regulation assembly, specifically the proximal gas outflow lumen 346 initially, thereby escaping the turbulent environment.

The vacuum pressure thus ultimately urges the outflowing contaminated gas to make an angled turn into the fluid regulation assembly 300, entering the proximal gas outflow lumen 346 which may comprise a smaller volume than the upper region of the evacuating gas conduit 340. The contaminated gas then flows through the reduced diameter flow regulation lumen 350, encountering the flow regulation lumen 350 and flowing therethrough at a variably selectable flow rate if the flow regulator 352 is actuated, i.e., in an "ON" position. Once through the flow regulation lumen 350, the contaminated gas then enters the distal gas outflow lumen 348 comprising a diameter larger than the diameter of the flow regulation lumen 350. Ultimately, the contaminated gas may be evacuated to a waste reservoir or otherwise disposed of.

As described, there are a series of rate and/or volume flow restriction elements in the duel lumen flow conduit embodiment of the present invention, each of which contributes reduction of flow rate from the external vacuum flow rate down to the desired range of 0 to 30 liters per minute within the body cavity at the plurality of gas evacuation ports. These restriction elements are described in co-pending application entitled "Device and Method for Evacuating Surgical Vapor and Mist From a Body Cavity", having Ser. No. 13/157,434 and filed on even date herewith, the entire contents of which are incorporated herein by reference. The flow regulation assembly assembly 300 is the flow restriction element of the series of restriction elements which allows infinitely variable selectivity of flow rates during the procedure, without changing any equipment as will be discussed further herein.

The combined effect of the described flow restriction elements of the present invention are to reduce the external vacuum flow rate to a safe, effective and efficient flow rate of between 0 to 30 liters per minute at the gas evacuation ports 124. As the skilled artisan will recognize, these flow restriction elements within the inventive system may be individually modified or attenuated to bring the system into compliance with the desired flow rate at the gas evacuation ports 124, i.e., within the preferred range of flow of between 0 to 30 liters per minute. The individual flow restriction elements work in harmony with each other to provide a systematic approach to the flow rate at the gas evacuation ports 124 and within the surgical cavity 6. Attenuation of the system however to an exact flow rate at any point during the procedure is made possible by the variably selectable actuation capabilities provided by the flow regulation assembly 300.

As the vacuum source is activated and the flow regulation assembly 300 is actuated, contaminated gas will begin traveling through the plurality of gas evacuation ports 224 which are disposed through the housing wall 212, allowing fluid communication between the lower portion of the single lumen 214 and the surgical cavity 6. As the evacuating gas enters the gas evacuation ports 224, it is then urged via vacuum pressure upward through the evacuating gas conduit. When the evacuating gas reaches the entry to the upper chamber 226, the structure and function of which is the same as that element 126 is discussed supra, it encounters a plurality of ports 229 that provide fluid communication with the lower portion of the single lumen 214, the gas evacuation ports 224, the surgical cavity 6 and the upper chamber 226. Since the upper chamber 226 is also in fluid communication with the external vacuum source, the evacuating gas is urged through the ports 229 from the lower portion of the single lumen 214 and into the upper chamber 226. It is at this point in this embodiment of the present invention that two separate lumens exist, the upper portion of the single lumen 216, i.e., that portion of the single lumen disposed above the apertures 218 and that serves only the function and purpose of a working channel for allowing instrument access to the surgical site 6 therethrough, and the evacuating gas conduit. The lower portion of the single lumen 214, i.e., that portion of the single lumen disposed below the apertures 218, performs both working channel for instrument access functions as well as gas evacuation functions; these functions are bifurcated at the apertures 218. Therefore, to this point the evacuating gas conduit comprises the plurality of gas evacuation ports 224 disposed in the lower portion of the single lumen, the lower portion of the single lumen 214, the plurality of apertures 218 that allow fluid communication with the lower portion of the single lumen 214 and the upper chamber 226, and the upper chamber 226.

The preferred single lumen in this alternate embodiment is sized to admit a 5 mm diameter instrument, though additional embodiments comprise a single lumen that can accommodate instruments therein that range from 3 mm to 14 mm in diameter, but this embodiment allows a space around the instrument within the single lumen for evacuation of contaminated gas. As those skilled in the art will readily recognize and as discussed supra, an elongate trocar sleeve 210 and the single lumen 214, both defined by housing 212, may also be adapted in length to accommodate certain procedures. For example, bariatric laparoscopic procedures may benefit from a longer trocar sleeve 210 and single lumen 214 according to the present invention's various embodiments. However, it is important to understand that the size and shape of the present invention is not limited to laparoscopy, e.g., and may, therefore, be adapted and used in other procedures in various embodiments of the present invention.

Figure 7:
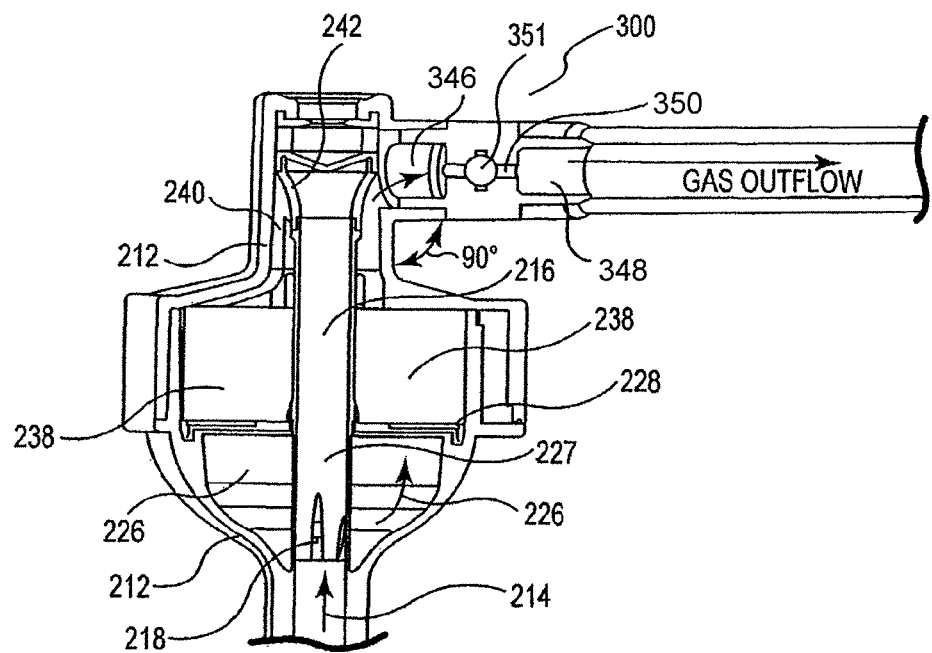
FIG. 7 is a side cross sectional and cutaway view of one embodiment of the present invention.

As shown in FIG. 7, this alternate embodiment comprises an evacuating gas conduit comprising a lumen having a lower portion 214 that serves dual functions as a working channel allowing instrument access as well as contaminated gas evacuation in response to a downstream vacuum source and an upper portion 216 that serves only working channel instrument access functions.

As the vacuum source is activated and the flow regulation assembly 300 is actuated, contaminated gas will begin traveling through the plurality of gas evacuation ports 224 which are disposed through the housing wall 212, allowing fluid communication between the lower portion of the single lumen 214 and the surgical cavity 6. As the evacuating gas enters the gas evacuation ports 224, it is then urged via vacuum pressure upward through the evacuating gas conduit. When the evacuating gas reaches the entry to the upper chamber 226, the structure and function of which is the same as that element 126 is discussed supra, it encounters a plurality of ports 228 that provide fluid communication with the lower portion of the single lumen 214, the gas evacuation ports 224, the surgical cavity 6 and the upper chamber 226. Since the upper chamber 226 is also in fluid communication with the external vacuum source, the evacuating gas is urged through the ports 228 from the lower portion of the single lumen 214 and into the upper chamber 226. It is at this point in this embodiment of the present invention that two separate lumens exist, the upper portion of the single lumen 216, i.e., that portion of the single lumen disposed above the apertures 218 and that serves only the function and purpose of a working channel for allowing instrument access to the surgical site 6 therethrough, and the evacuating gas conduit. The lower portion of the single lumen 214, i.e., that portion of the single lumen disposed below the apertures 218, performs both working channel for instrument access functions as well as gas evacuation functions; these functions are bifurcated at the apertures 218. Therefore, to this point the evacuating gas conduit comprises the plurality of gas evacuation ports 224 disposed in the lower portion of the single lumen, the lower portion of the single lumen 214, the plurality of apertures 218 that allow fluid communication with the lower portion of the single lumen 214 and the upper chamber 226, and the upper chamber 226.

The evacuating gas will eventually find an outlet from the turbulent environment in the upper region of the evacuating gas conduit 240. A flow regulation assembly 300 is in operative and fluid connection and communication with the upper region of the evacuating gas conduit 240, at an angled connection, the preferred connection will comprise substantially a right angle as illustrated, though other angled connections are within the scope of the present invention. The fluid regulation assembly 300 comprises a proximal gas outflow lumen 346 and a distal gas outflow lumen 348, each comprising a diameter and a flow regulator lumen 350 disposed between the proximal and distal gas outflow lumens 346, 348 and further comprising a diameter. The flow regulation lumen 350 diameter is smaller than both of the diameters of the proximal and distal gas outflow lumens 346, 348. The flow regulation lumen 350 is in operative and fluid communication with the proximal and distal outflow lumens 346, 348. See also FIG. 5 and the accompanying discussion supra.

A filtration element 238 having a height and comprising a material well known to the skilled artisan that assists in removing contaminants from the evacuating gas and also serves as a restrictive device to reduce the flow rate of the evacuating gas. In one embodiment, the filtration element 238 comprises smoke filtering charcoal elements. The pressure drop across the filtration element 238 may be tuned in order to change the balance between contaminant filtration and gas evacuation flow rates. In another embodiment, the filtration element 238 may also comprise an anti-microbial and/or anti-bacterial layer or, alternatively, such materials may be integrated into and throughout the filtration element. The levels of filtration of these additional anti-microbial and/or anti-bacterial materials may be attenuated in order to produce the specifically desired flow rate at a specific external vacuum pressure. The evacuating gas conduit thus further comprises the filtration element 238.

The evacuating gas exits the filtration element 238 and enters the upper region of the evacuating gas conduit 240. The upper portion of the single lumen 216 comprises a radiused or curved section 242 which directs the evacuating gas radially outward toward the trocar housing 212, thereby slowing the flow rate of the evacuating gas and generating a turbulent environment as this radially directed gas impacts the housing wall 212 and rebounds therefrom and flowing directly or indirectly into the oncoming evacuating gas that has exited from the filtration element. This turbulence further slows the flow rate of the evacuating gas. The evacuating gas conduit thus further comprises the upper region of the evacuating gas conduit 240.

The evacuating gas will eventually find an outlet from the turbulent environment in the upper region of the evacuating gas conduit 240. A flow regulation assembly 300 is in operative and fluid connection and communication with the upper region of the evacuating gas conduit 240, at an angled connection, the preferred connection will comprise substantially a right angle as illustrated, though other angled connections are within the scope of the present invention. The fluid regulation assembly 300 comprises a proximal gas outflow lumen 346 and a distal gas outflow lumen 348, each comprising a diameter and a flow regulator lumen 350 disposed between the proximal and distal gas outflow lumens 346, 348 and further comprising a diameter. The flow regulation lumen 350 diameter is smaller than both of the diameters of the proximal and distal gas outflow lumens 346, 348. The flow regulation lumen 350 is in operative and fluid communication with the proximal and distal outflow lumens 246, 248. See also FIG. 5 and the accompanying discussion supra.

Disposed within the flow regulator lumen 350 is a flow regulator 351 that may be actuated to allow, or prevent, fluid communication with the gas evacuation ports 224 and surgical cavity 6 and a downstream external vacuum and to allow fluid communication through the system to the gas evacuation ports 224 and the surgical cavity 6 as described herein. Thus, the flow regulation assembly 300 of the present invention provides a plurality of "ON" settings comprising selectable "LOW" flow rate and "MAX" flow rate settings, with an infinitely variable selectable flow rates therebetween, designated herein as "MID" flow rate settings. The flow regulation assembly 300 will be discussed further infra as it applies to both the dual and single lumen embodiments illustrated and discussed herein.

Figure 6:
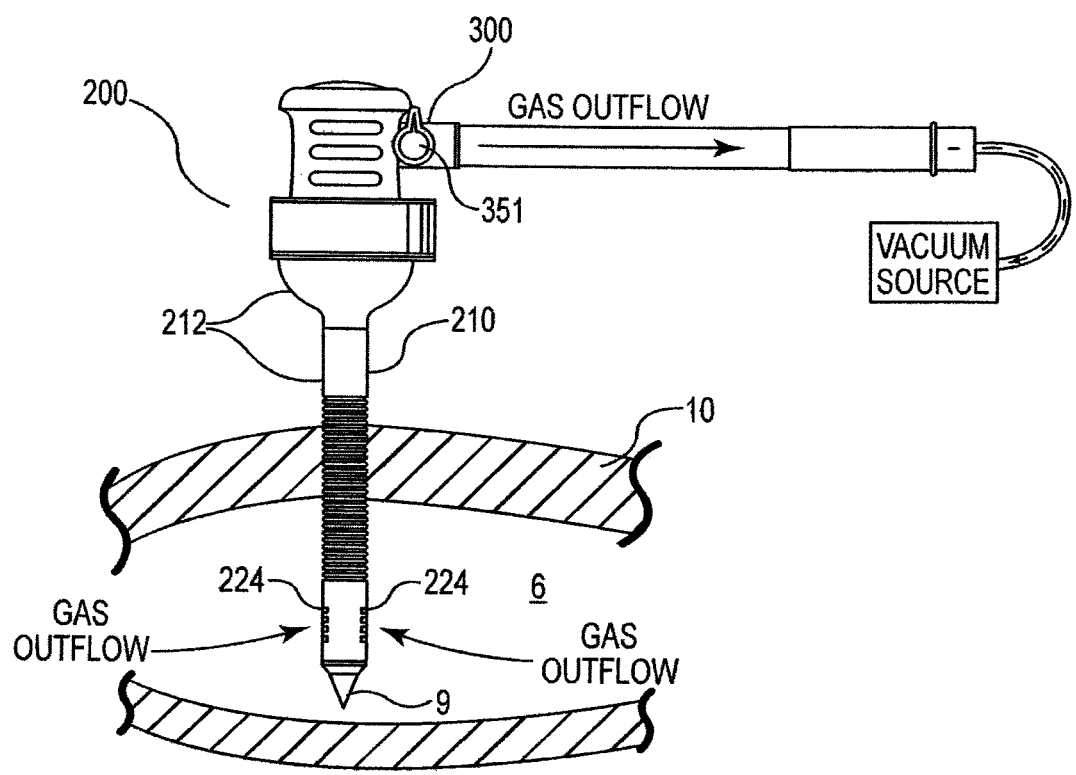
FIG. 6 is a side view of one embodiment of the present invention.
Figure 8:
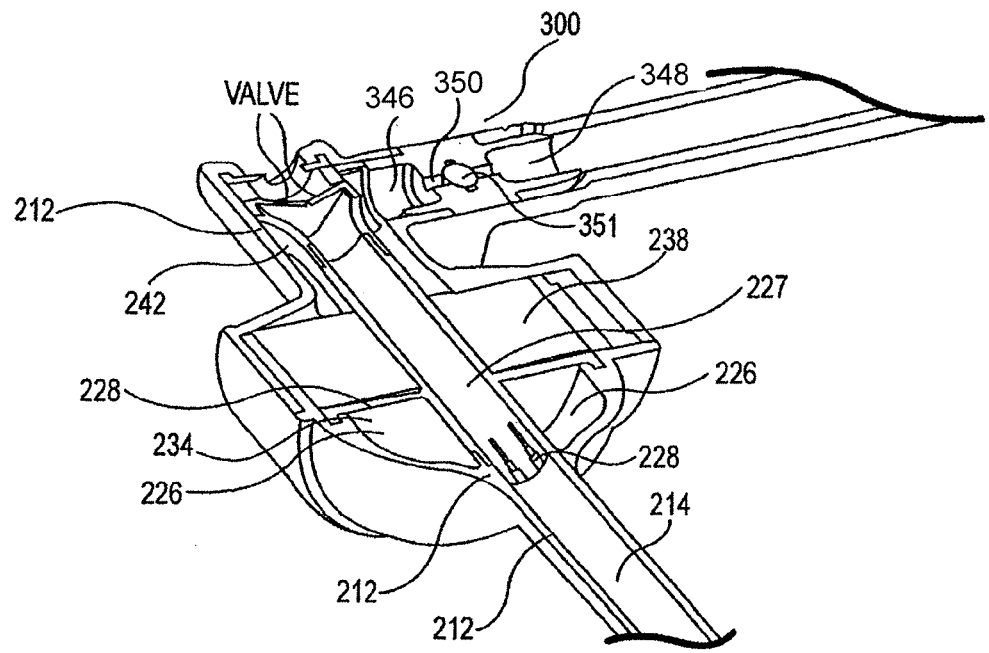
FIG. 8 is a perspective cross sectional and cutaway view of one embodiment of the present invention.

Thus, the single lumen embodiment illustrated in FIGS. 6-8 provide an evacuating gas conduit that provides a pathway for the evacuating gas from the bodily cavity 6 to a container (not shown) for proper disposal, driven by vacuum pressure provided by an external vacuum source in fluid communication and operative connection with the evacuating gas conduit. The structures along the evacuating gas conduit provide for an overall flow rate reduction at the gas evacuation ports 224 and within the surgical cavity 6, necessary to prevent unwanted and potentially damaging effects that may be induced by the relatively high pressure of the external vacuum source.

The evacuating gas conduit begins at the gas evacuation ports 224 where the contaminated gas enters the trocar sleeve 210 at the plurality of gas evacuation ports 224 shown as disposed generally on the distal end of the lower portion of the single lumen 214 in response to a vacuum pressure applied at the downstream end of the gas evacuating gas conduit. The gas evacuation ports 224 may be distributed at other locations along the elongate trocar sleeve 210 and, therefore, are not restricted to the distal end of the lower portion of the single lumen 214

After the elongated trocar sleeve 210 is positioned within a surgical cavity 6 and the surgeon determines the necessity of clearing the surgical cavity of contaminants generated during cutting and the like, the gas evacuating conduit may be actuated by moving the flow regulation assembly 300 to an "ON" position and starting or turning on the external vacuum to cause a vacuum airflow through the evacuating gas conduit.

First, in response to the vacuum pressure, the evacuating gas is urged into the plurality of gas evacuation ports 224 and into the lower portion of the single lumen 214 which comprises substantially constant diameter and volume, wherein the gas is urged upward through the constant diameter region until reaching the plurality of apertures 218 disposed between the upper chamber 226 and the lower portion of the single lumen 214, allowing fluid communication therebetween. The upper chamber 226 comprises a volume that is larger than the volume of the lower portion of the single lumen 214, particularly when an instrument is disposed therein. The enlarged upper chamber 226 comprises the restrictor plate 228 comprising a central through-hole or aperture 227 for the working channel to pass through and a plurality, or at least one, of the restrictor plate flow ports) 234.

As the evacuating gas is urged via the external vacuum source further downstream within the evacuating gas conduit, passing through the restrictor plate flow ports) 234, it encounters a gas filtration element 238 which further impedes the contaminated gas flowing therethrough. After exiting the gas filtration element 238, the evacuating gas enters the upper region of the evacuating gas conduit 240 and ultimately generating a turbulent environment as the gas encounters the upper portion of the single lumen 216, in particular the radiused or curved section 242, and is radially urged against the trocar housing wall 212, rebounding from that impact only to encounter incoming evacuating gas exiting from the filtration element 238. Ultimately, the gas finds a release from this turbulent environment through the flow regulation assembly 300, which is in operative and fluid communication and connection with the upper region of the evacuating gas conduit 240. As can be seen in FIG. 8, as well as the embodiment of FIG. 3 which shares this structural feature, some of the evacuating gas that encounters the curved surface of the upper portion of the single lumen 242 will be urged radially into the flow regulation assembly 300, thereby escaping the turbulent environment.

We turn now to the flow regulation assembly 300, as illustrated in relation to the embodiments 100 and 200 and as shown in detail in FIGS. 9-13B. The flow regulation assembly 300 is in operative and fluid communication and operative connection with the upper region 140 of the secondary lumen 122 as illustrated in connection with embodiment 100. The flow regulation assembly 300 is in operative and fluid communication and operative connection with the upper region of the evacuating gas conduit 240 of embodiment 200.

Thus, there are a series of rate and/or volume flow restriction elements in the single lumen evacuating gas conduit embodiment 200 of the present invention, each of which contributes reduction of flow rate from the external vacuum flow down to the desired range of 0 to 30 liters per minute within the body cavity at the plurality of gas evacuation ports 224.

The combined effect of the described flow restriction elements of this embodiment 200 of the present invention are to reduce the relatively high external vacuum flow rate to a safe, effective and efficient flow rate of between 0 to 30 liters per minute or more preferably between 6 to 30 liters per minute at the gas evacuation ports. As the skilled artisan will recognize, these flow restriction elements may be individually modified or attenuated to bring the system into compliance with the desired flow rate at the gas evacuation ports 224, i.e., within a preferred range of flow of, e.g., between 0 to 30 liters per minute. The individual flow restriction elements work in harmony with each other to provide a systematic approach to the flow rate at the gas evacuation ports 224 and within the surgical cavity 6. Infinitely selectable attenuation of the flow rate is made possible by the flow regulation assembly 300 and in particular the flow regulator's variable positioning in an "ON" position. Further, as the skilled artisan will recognize, a much tighter range of flow, e.g., 6 to 10 liters per minute or 25 to 30 liters per minute or any range of flow therebetween, may be obtained through manipulation of the individual flow restriction elements, the actual targeted flow rate will depend on the desired evacuation time and flow.

We turn now to the flow regulation assembly 300, as illustrated in relation to the embodiments 100 and 200 and as shown in detail in FIGS. 9-13B. The flow regulation assembly 300 is in operative and fluid communication and operative connection with the upper region of the secondary lumen 140 as illustrated in connection with embodiment 100. The flow regulation assembly 300 is in operative and fluid communication and operative connection with the upper region of the evacuating gas conduit 240 of embodiment 200.

In both illustrated embodiments 100 and 200, the flow regulation assembly 300 provides an infinitely variable flow rate selection method and device with an infinite and selectable range of "ON" settings located between a "LOW" and a "MAX" setting, as well as an "OFF" setting within the illustrated systems and embodiments.

In all embodiments described herein, the flow regulation assembly 300 of the present invention comprises, in one embodiment, a proximal gas outflow lumen 346 having a diameter and a distal gas outflow lumen 348 having a diameter, wherein the proximal and distal gas outflow lumens 346, 348 are substantially similar in diameter. Disposed between the proximal and distal gas outflow lumens 346, 348 is the flow regulation lumen 350, all of which are defined within the flow regulation housing. The flow regulation housing further defines a flow adjuster lumen 354 which is disposed at an angle, preferably 90 degrees though other angles will suffice, to the proximal and distal gas outflow lumens 346, 348 and the flow regulation lumen 350 therebetween. The flow adjuster lumen 354 engages and intersects the flow regulation lumen 350 as illustrated by the broken lines of FIG. 10 and comprises an open first end and a closed opposing end as illustrated.

Flow regulation assembly 300 further comprises a flow rate adjuster 356 comprising a generally cylindrical profile, a variable orifice 358, side shoulder elements 359 which extend radially outwardly from the generally cylindrical profile and a locating notch 361 in the top portion of the flow rate adjuster 356, a biased adjuster return spring 360, a seal 362 which sealingly slides down the cylindrical surface of the adjuster 356 to rest upon the shoulders 359 and which seals, e.g., screwingly seals, to a threaded portion 363 at the open top of the flow regulation housing proximal to the flow adjuster lumen, and a rotatable adjuster knob 364 comprising a complementary male element, not shown but which is well known in the art and which comprises a shape complementary notch 361. Thus, when seal 362 is screwed or otherwise sealed to the threaded portion 363, the biasing spring 360 presses the adjuster 356 upwardly toward the seal 362 element, but is prevented from ejecting the spring 356 from the flow adjuster lumen 354 by the engagement of the shoulders 359 against the seal element 362. The portion of the adjuster above the shoulders 359 at least partially extends above the seal to allow axial movement, i.e., translation, of the adjuster 356 downward into the lumen 354 by pressing on the rotator adjustment knob 364. Easing or releasing the downward pressure on the rotator adjustment knob 364 results in axial translation of the adjuster upward in lumen 354.

Thus, the adjuster 356 may be axially translated within the flow adjuster lumen 354 by applying varying degrees of pressure to the rotator adjustment knob 364 further into the lumen 354. Sufficient pressure must be applied to overcome the biasing force of spring 360. The adjuster 356 may also be rotated within lumen 354 by turning the rotator adjustment knob 364. Rotation of the adjuster 356 will either align the flow regulation lumen 350 with the variable orifice 358, allowing a flow rate of evacuating gas therethrough, or remove the alignment of the flow regulation lumen 350 and the variable orifice 358, thereby stopping the flow of evacuating gas altogether.

The variable orifice 358 comprises a shaping wherein the lower region 365 of the orifice has the smallest volume and wherein the orifice becomes progressively larger in volume moving upward on the orifice 358. Ultimately, the largest volume region of the orifice 358 is found at the top region 367 of the orifice 358, with progressively smaller volumes between top region 367 and lower region 365.

Figure 9:
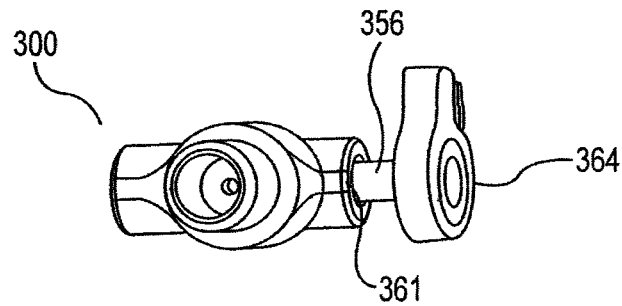
FIG. 9 is a side perspective cutaway view of one embodiment of the flow control adjuster of the present invention, positioned in the "OFF" position.
Figure 10:
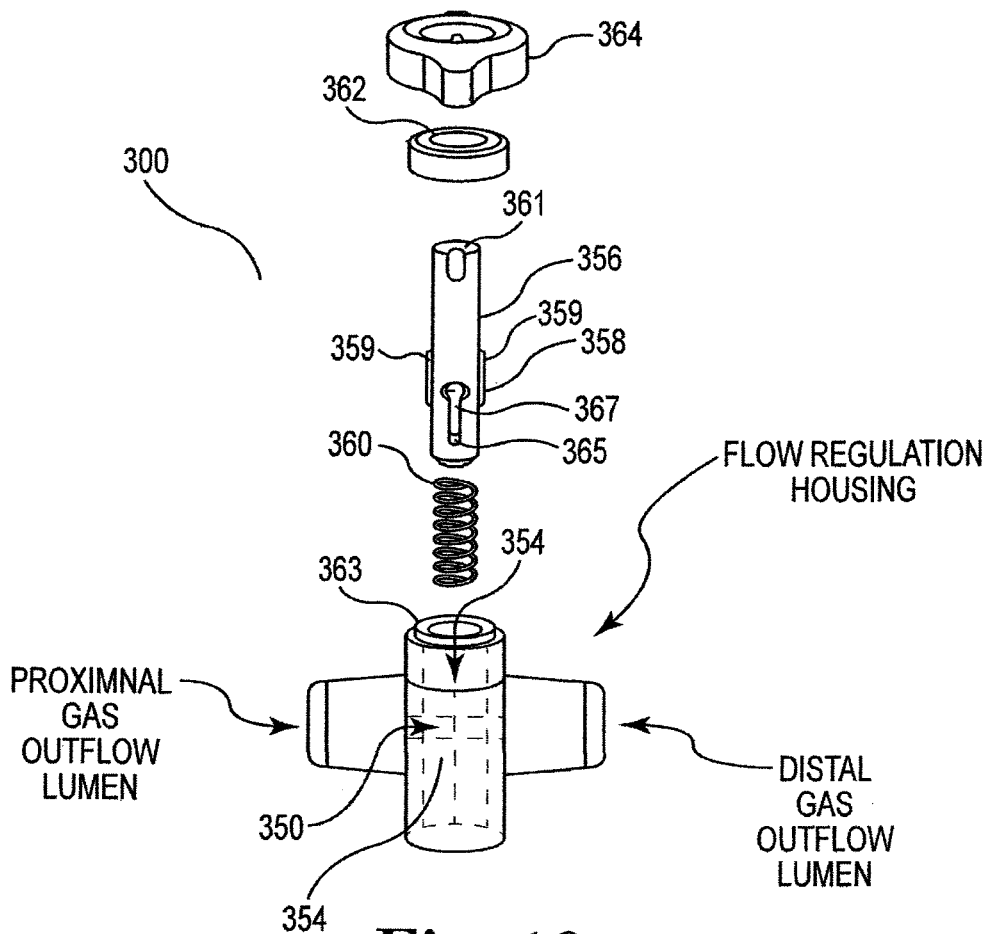
FIG. 10 is an exploded top view of one embodiment of the flow control adjuster of the present invention, positioned in the "OFF" position.

When the variable orifice 358 is rotated out of alignment with the flow regulation lumen 350, flow is prevented through the flow regulation assembly 300 and, as a result, no flow may be achieved at gas evacuation ports 124 of embodiment 100 or gas evacuation ports 224 of embodiment 200. This setting comprises the "OFF" position. FIGS. 9 and 10 illustrate the flow regulation assembly in the "OFF" position, with the variable orifice 358 rotated out of alignment with the flow regulation lumen 350.

Figure 11A:
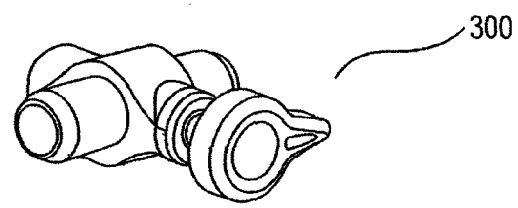
FIG. 11A is a cutaway perspective view of one embodiment of the flow control adjuster of the present invention, positioned in a "LOW" position.
Figure 11B:
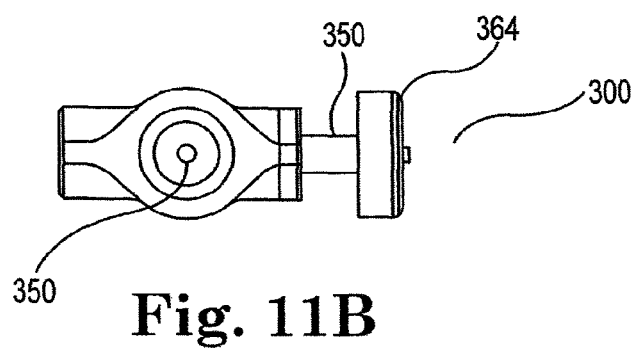
FIG. 11B is a side cutaway view of one embodiment of the flow control adjuster of the present invention, positioned in a "LOW" position.

When the variable orifice 358 is rotated into alignment with the flow regulation lumen 350, the orifice 358 aligns its lower region 365, wherein the lowest amount of flow through of evacuating gas is allowed with the flow regulation lumen 350. This setting is an "ON" position and comprises "LOW" in the situation where no axial translation of the adjuster 356 is present, and may comprise in one embodiment about 6 liters per minute. Other "LOW" flow rates may be achieved as the skilled artisan will readily understand by, inter alia, modifying the diameter of lower region 365 of the orifice 358 and/or modifying the external vacuum pressure and resulting flow rate accordingly. FIGS. 11A and 11B illustrate one embodiment of the "LOW" position, wherein the lower region 365 of the orifice 358 is rotated into alignment with the flow regulation lumen 350, i.e., the adjuster 365 is not translated downwardly into lumen 354 any distance. The variable orifice 358 obstructs the flow regulation lumen 350 to a predetermined degree in the "LOW" position, effectively decreasing the volume of evacuating gas flowing therethrough.

Figure 12A:
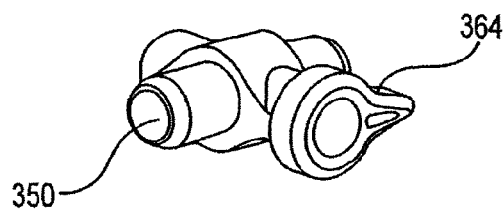
FIG. 12A is a cutaway perspective view of one embodiment of the flow control adjuster of the present invention, positioned in a "MAX" position.
Figure 12B:
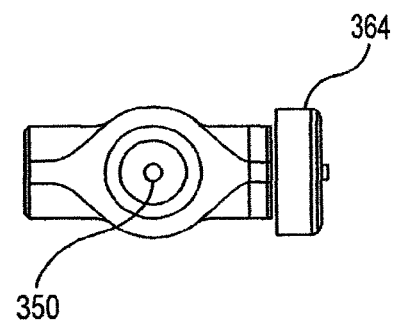
FIG. 12B is a side cutaway view of one embodiment of the flow control adjuster of the present invention, positioned in a "MAX" position.

Application of downward pressure to the knob 364 will, as described, cause the adjuster 356 to translate downwardly into the lumen. If the variable orifice is in alignment with the flow regulation lumen 350 and the adjustor 356 is translated fully downwardly into the lumen 350, the flow regulation lumen 350 is in fluid communication with the upper region 367 of the variable orifice 358, thereby allowing the maximum flow rate therethrough which comprises the setting "MAX" and may comprise in one embodiment about 17 liters per minute. Other "MAX" flow rates may be achieved as the skilled artisan will readily understand by, inter alia, modifying the diameter of upper region 367 of the orifice 358 and/or modifying the external vacuum pressure and resulting flow rate accordingly. FIGS. 12A and 12B illustrate one embodiment of the "MAX" position, wherein the upper region 367 of the variable orifice 358 is rotated into alignment with the flow regulation lumen 350, i.e., the adjuster 365 is completely translated downwardly into lumen 354 thereby exposing the largest volume region of the orifice 358 to the flow regulation lumen 350. Thus, "MAX" may comprise the fluid regulation lumen 350 being wholly unobstructed.

An infinite number of operator-selectable "ON" positions, comprising "LOW" and "MAX" and any flow rate therebetween is provided by the present invention. The infinite selectivity of flow rate between "LOW" and "MAX" is provided by the smoothly gradual increase in volume of the variable orifice 358 from the lower region 365 to the upper region 367. As the adjustor 356, comprising the variable orifice 358, is translated axially downward into lumen 354, an infinite number of translating positions are achieved, each translating position comprising a slightly different volume of orifice 358 exposed to and in alignment with fluid regulation lumen 350. The more axial translation, the greater the volume. In the exemplary embodiment, therefore, the operator may choose from "OFF" or "ON", wherein the "ON" may, in this non-limiting example, comprise any flow rate from 6 liters per minute to 17 liters per minute. Effectively, this flow rate reduction and selection is a significant restriction element which, in combination with the flow restriction elements described supra, allows reduction of the relatively high flow rates of the external vacuum to between, e.g., 6 lpm to 17 lpm within the surgical cavity. The skilled artisan will recognize that the "MAX", "LOW" and "ON" flow rates may be modified according to the present invention as needed or desired. The flow rate values presented herein are purely for exemplary purposes and are not limiting in any respect. Alternate flow rate values for, inter alia, "MAX, "LOW" and "ON" may therefore be readily recognized by the skilled artisan; each such alternate flow value is within the scope of the present invention.

The present invention should not be considered limited to the particular examples described above, but rather should be understood to cover all aspects of the invention. Various modifications, equivalent processes, as well as numerous structures to which the present invention may be applicable will be readily apparent to those of skill in the art to which the present invention is directed upon review of the present specification.

What is claimed is:

1. A device for safe, effective and efficient evacuating of contaminated insufflated gas from a surgical cavity comprising:
    a housing defining an elongate trocar sleeve having a distal tapered section;
    a working channel defined within the trocar sleeve, comprising an upper portion of a single lumen, wherein the upper portion of the single lumen functions as a working channel to allow access for instruments to the surgical cavity through the single lumen;
    a gas evacuating conduit; comprising
        a lower portion of the single lumen, the lower portion of the single lumen functioning as a working channel to allow access for instruments to the surgical cavity through the single lumen and also functioning to evacuate contaminated gas from the surgical cavity,
        a plurality of gas evacuation ports disposed through the trocar sleeve in the lower portion of the single lumen and allowing fluid communication between the surgical cavity and the lower portion of the single lumen,
        an upper chamber in fluid communication with the lower portion of the single lumen, the upper chamber having a volume that is larger than a volume of the single lumen,
        a plurality of apertures disposed between the upper chamber and the lower portion of the single lumen, allowing fluid communication therebetween,
        a restrictor plate having an upper and lower surfaces and comprising a plurality of restrictor plate ports therethrough within the upper chamber, the restrictor plate ports allowing fluid communication between the upper chamber and an upper region of the gas evacuating conduit,
        a filtration element disposed on the upper surface of the restrictor plate and within the upper chamber,
        the upper region of a gas evacuating conduit in fluid communication with the upper chamber and defined by the trocar sleeve housing and the working channel wherein the working channel comprises a radiused curved section for directing evacuating gas radially outward against the trocar sleeve housing within the upper region of the gas evacuating conduit and creating a turbulent environment, and
    a flow regulation assembly in fluid communication and operative angled connection with the upper region of the gas evacuating conduit comprising:
        a flow regulation housing defining
            a proximal gas outflow lumen having a diameter,
            a distal gas outflow lumen having a diameter,
            a flow regulation lumen disposed between the proximal and distal gas outflow lumens diameter that is less than the diameters of the distal and proximal gas outflow lumens, and
            a flow adjuster lumen, disposed at an angle to the proximal and distal gas outflow lumens and the flow regulation lumen, the flow adjuster lumen intersecting the flow regulation lumen and having an open top, a threaded portion proximal the open top and a closed bottom;
        a flow rate adjuster comprising
            a generally cylindrical profile,
            a variable orifice therethrough and having a top portion and a lower portion, wherein the volume of the variable orifice is largest at the top portion of the variable orifice and lowest at the lower portion of the variable orifice,
            side shoulder elements extending radially outward from the generally cylindrical profile,
            a locating notch disposed in the top portion of the generally cylindrical flow rate adjuster profile,
            a biased adjuster return spring;
            a seal, comprising complementary threads to sealingly engage the threaded portion of the flow adjuster lumen;
            an adjustment knob comprising a male element complementary in shape to the locating notch disposed in the top portion of the generally cylindrical flow rate adjuster profile for engagement therein,
    wherein the flow rate adjuster may be rotated to an "OFF" position wherein the variable orifice is not in alignment with the flow regulation lumen, a "LOW" position, wherein the variable orifice is rotated into alignment with the flow regulation lumen with no axial translation of the flow rate adjuster within the flow adjuster lumen, to a "MAX" wherein the variable orifice is rotated into alignment with the flow regulation lumen and with full axial translation of the flow rate adjuster within the flow adjuster lumen, or to any "ON" position between "LOW" and MAX", wherein the variable orifice is rotated into alignment with the flow regulation lumen and the flow rate adjuster comprises an axial translation at a selected point between no translation and full translation within the flow adjuster lumen an external vacuum source in operative connection and actuable fluid communication with the flow regulation conduit, the upper region of the gas evacuating conduit, the filtration element, the restrictor plate ports, the upper chamber, the single lumen, the gas evacuation ports and the surgical cavity.

2. The device of claim 1, wherein the operative angled connection of the fluid regulation assembly with the upper region of the gas evacuating conduit is substantially 90 degrees.

3. The device of claim 1, wherein the operative angled connection of the fluid regulation assembly with the upper region of the secondary lumen comprises an acute angle.

4. The device of claim 1, wherein the operative angled connection of the fluid regulation conduit with the upper region of the secondary lumen comprises an obtuse angle.

5. A trocar for selectively and simultaneously providing instrument access to a surgical cavity and allowing for evacuating contaminated gas from the surgical cavity, comprising:
a working channel to allow access for instruments to the surgical cavity;
a gas evacuating conduit in fluid communication with the surgical cavity; and
a flow regulation assembly in fluid communication with the gas evacuating conduit and comprising:
a flow adjuster lumen arranged at an angle to flow of gas in the gas evacuating conduit;
a flow rate adjuster arranged in the flow adjuster lumen and comprising:
a generally cylindrical profile,
a variable orifice therethrough and having a top portion and a lower portion, wherein the volume of the variable orifice is largest at the top portion of the variable orifice and lowest at the lower portion of the variable orifice,
side shoulder elements extending radially outward from the generally cylindrical profile,
a locating notch disposed in the top portion of the generally cylindrical flow rate adjuster profile,
a biased adjuster return spring;
a seal, comprising complementary threads to sealingly engage the threaded portion of the flow adjuster lumen; and
an adjustment knob comprising a male element complementary in shape to the locating notch disposed in the top portion of the generally cylindrical flow rate adjuster profile for engagement therein,
wherein the flow rate adjuster may be rotated to an "OFF" position wherein the variable orifice is not in alignment with the flow regulation lumen, to a "LOW" position, wherein the variable orifice is rotated into alignment with the flow regulation lumen with no axial translation of the flow rate adjuster within the flow adjuster lumen, to a "MAX" position wherein the variable orifice is rotated into alignment with the flow regulation lumen and with full axial translation of the flow rate adjuster within the flow adjuster lumen, or to any "ON" position between "LOW" and MAX", wherein the variable orifice is rotated into alignment with the flow regulation lumen and the flow rate adjuster comprises an axial translation at a selected point between no translation and full translation within the flow adjuster lumen.

6. A trocar for selectively and simultaneously providing instrument access to a surgical cavity and allowing for evacuating contaminated gas from the surgical cavity, comprising:
a working channel to allow access for instruments to the surgical cavity;
a gas evacuating conduit in fluid communication with the surgical cavity; and
a flow regulation assembly in fluid communication with the gas evacuating conduit and comprising:
a flow adjuster lumen arranged at an angle to flow of gas in the gas evacuating conduit;
a flow rate adjuster arranged in the flow adjuster lumen and comprising:
a generally cylindrical profile adapted to selectively rotate and translate within the flow adjuster lumen;
an orifice extending through the generally cylindrical profile and having a first end and a second end, wherein a size of the orifice increases from the first end to the second end; and
a biasing element arranged to bias the generally cylindrical profile along the flow adjuster lumen to a position where the position of the first end of the orifice is arranged substantially at a center of the gas evacuating conduit,
wherein:
the generally cylindrical profile may be rotated between an "OFF" position where the orifice is not exposed to gas in the gas evacuating conduit and an "ON" position where a portion of the orifice is substantially aligned with the flow of gas in the gas evacuating conduit; and
the generally cylindrical profile may be selectively and actively translated against the biasing element such that other portions of the orifice are substantially aligned with the flow of gas in the gas evacuating conduit thereby allowing for active on-demand adjustment of the flow between a "LOW" flow condition, a "MAX" flow condition, and any flow condition therebetween.

* * * * *